(12) United States Patent
Martinek et al.

(10) Patent No.: US 8,403,957 B2
(45) Date of Patent: Mar. 26, 2013

(54) CANNULATED SUTURE ANCHOR SYSTEM

(75) Inventors: Jonathan Martinek, Chesire, CT (US); Richard Lehman, St. Louis, MO (US)

(73) Assignee: Covidien LP, Mansfield, MA (US)

( * ) Notice: Subject to any disclaimer, the term of this patent is extended or adjusted under 35 U.S.C. 154(b) by 1047 days.

(21) Appl. No.: 12/137,123

(22) Filed: Jun. 11, 2008

(65) Prior Publication Data

US 2008/0243184 A1 Oct. 2, 2008

Related U.S. Application Data

(63) Continuation of application No. 11/371,754, filed on Mar. 9, 2006, now abandoned.

(51) Int. Cl.
*A61B 17/04* (2006.01)
(52) U.S. Cl. ..................................................... 606/232
(58) Field of Classification Search .................. 606/232, 606/73, 300, 301, 304, 305, 233, 306–321
See application file for complete search history.

(56) References Cited

U.S. PATENT DOCUMENTS

| | | | |
|---|---|---|---|
| 4,259,072 A | 3/1981 | Hirabayashi et al. | |
| 4,454,875 A | 6/1984 | Pratt et al. | |
| 4,570,623 A | 2/1986 | Ellison et al. | |
| 4,738,255 A | 4/1988 | Goble et al. | |
| 4,772,286 A | 9/1988 | Goble et al. | |
| 4,870,957 A | 10/1989 | Goble et al. | |
| 4,895,148 A | 1/1990 | Bays et al. | |
| 4,927,421 A | 5/1990 | Goble et al. | |
| 4,950,270 A | 8/1990 | Bowman et al. | |
| 5,013,316 A | 5/1991 | Goble et al. | |
| 5,019,080 A | 5/1991 | Hemer | |
| 5,100,417 A * | 3/1992 | Cerier et al. | 606/139 |
| 5,122,133 A | 6/1992 | Evans | |
| 5,156,616 A | 10/1992 | Meadows et al. | |
| 5,176,682 A | 1/1993 | Chow | |

(Continued)

FOREIGN PATENT DOCUMENTS

| | | |
|---|---|---|
| JP | 8-24281 A | 1/1996 |
| JP | 8-66410 A | 3/1996 |

(Continued)

OTHER PUBLICATIONS

International Search Report from European Application No. EP 08021283.0 dated Feb. 24, 2009.

(Continued)

*Primary Examiner* — Gary Jackson
*Assistant Examiner* — Lindsey Bachman

(57) ABSTRACT

A system and associated method for arthroscopic repair is particularly adapted in reattaching a ligament and/or tendon to cortical bone of the shoulder. A suture anchor system includes a suture anchor, preferably, a screw anchor, and an installation tool for installing the suture anchor in tissue. The suture anchor defines a longitudinal axis and has a longitudinal cannulation for reception and passage of a guide wire. The suture anchor has trailing and leading ends, and an anchor head adjacent the trailing end thereof. The anchor head includes at least one eyelet for reception of a suture and an internal bore therein. The installation tool includes a main body and a driver head extending from the main body. The main body includes an outer surface having a longitudinal recess therein to accommodate the suture. The driver head is correspondingly dimensioned to be received within the internal bore of the anchor head of the suture anchor whereby movement of the installation tool about a longitudinal axis, e.g., rotational movement, thereof causes corresponding movement, e.g., rotational, of the suture anchor. The installation tool may also define a longitudinal cannulation for reception and passage of the guide wire.

10 Claims, 5 Drawing Sheets

U.S. PATENT DOCUMENTS

| | | |
|---|---|---|
| RE34,293 E | 6/1993 | Goble et al. |
| 5,258,001 A | 11/1993 | Corman |
| 5,258,016 A | 11/1993 | DiPoto et al. |
| 5,320,115 A | 6/1994 | Kenna |
| 5,354,298 A | 10/1994 | Lee et al. |
| 5,370,662 A | 12/1994 | Stone et al. |
| 5,372,599 A | 12/1994 | Martins |
| 5,383,878 A | 1/1995 | Roger et al. |
| 5,387,129 A | 2/1995 | Hotea |
| RE34,871 E | 3/1995 | McGuire et al. |
| 5,417,712 A | 5/1995 | Whittaker et al. |
| 5,425,733 A | 6/1995 | Schmieding |
| 5,443,482 A | 8/1995 | Stone et al. |
| 5,443,509 A | 8/1995 | Boucher et al. |
| 5,456,685 A | 10/1995 | Huebner |
| 5,472,452 A | 12/1995 | Trott |
| 5,480,403 A | 1/1996 | Lee et al. |
| 5,522,845 A | 6/1996 | Wenstrom, Jr. |
| 5,571,139 A | 11/1996 | Jenkins, Jr. |
| 5,573,548 A | 11/1996 | Nazre et al. |
| 5,584,835 A | 12/1996 | Greenfield |
| 5,584,836 A | 12/1996 | Ballintyn et al. |
| 5,603,716 A | 2/1997 | Morgan et al. |
| 5,645,547 A | 7/1997 | Coleman |
| 5,690,676 A | 11/1997 | DiPoto et al. |
| 5,702,397 A | 12/1997 | Goble et al. |
| 5,718,706 A | 2/1998 | Roger |
| 5,733,307 A | 3/1998 | Dinsdale |
| 5,782,866 A | 7/1998 | Wenstrom, Jr. |
| 5,824,011 A | 10/1998 | Stone et al. |
| 5,871,504 A | 2/1999 | Eaton et al. |
| 5,885,294 A | 3/1999 | Pedlick et al. |
| 5,904,704 A | 5/1999 | Goble et al. |
| 5,911,721 A | 6/1999 | Nicholson et al. |
| 5,941,882 A | 8/1999 | Jammet et al. |
| 5,944,724 A | 8/1999 | Lizardi |
| 5,948,000 A | 9/1999 | Larsen et al. |
| 5,948,001 A | 9/1999 | Larsen |
| 5,980,559 A | 11/1999 | Bonutti |
| 5,993,451 A | 11/1999 | Burkhart |
| 6,045,573 A | 4/2000 | Wenstrom, Jr. et al. |
| 6,096,060 A | 8/2000 | Fitts et al. |
| 6,117,162 A | 9/2000 | Schmieding et al. |
| 6,139,565 A | 10/2000 | Stone et al. |
| 6,146,407 A | 11/2000 | Krebs |
| 6,146,408 A | 11/2000 | Bartlett |
| 6,149,669 A | 11/2000 | Li |
| 6,214,031 B1 | 4/2001 | Schmieding et al. |
| 6,235,057 B1 | 5/2001 | Roger et al. |
| 6,336,940 B1 | 1/2002 | Graf et al. |
| 6,371,124 B1 | 4/2002 | Whelan |
| 6,436,100 B1 | 8/2002 | Berger |
| 6,436,124 B1 | 8/2002 | Anderson et al. |
| 6,461,373 B2 | 10/2002 | Wyman et al. |
| 6,517,542 B1 | 2/2003 | Papay et al. |
| 6,629,977 B1 | 10/2003 | Wolf |
| 6,666,877 B2 | 12/2003 | Morgan et al. |
| 6,827,722 B1 * | 12/2004 | Schoenefeld ................. 606/104 |
| 6,840,953 B2 | 1/2005 | Martinek |
| 2001/0041937 A1 | 11/2001 | Rieser et al. |
| 2002/0032466 A1 | 3/2002 | Grafton et al. |
| 2002/0147463 A1 * | 10/2002 | Martinek ..................... 606/232 |
| 2002/0161401 A1 | 10/2002 | Steiner |
| 2003/0065361 A1 | 4/2003 | Dreyfuss |
| 2003/0125749 A1 | 7/2003 | Yuan et al. |
| 2003/0130695 A1 | 7/2003 | McDevitt et al. |
| 2003/0144696 A1 | 7/2003 | Sinnott et al. |
| 2004/0097945 A1 | 5/2004 | Wolf |
| 2005/0288682 A1 | 12/2005 | Howe |
| 2007/0005069 A1 * | 1/2007 | Contiliano et al. ............. 606/73 |

FOREIGN PATENT DOCUMENTS

| | | |
|---|---|---|
| JP | 9-24051 A | 1/1997 |
| JP | 2002-527121 A | 8/2002 |
| JP | 2006-6955 A | 1/2006 |
| WO | WO 2004/062507 | 7/2004 |
| WO | WO 2005/102190 A2 | 11/2005 |

OTHER PUBLICATIONS

Japanese Office Action with English Translation issued Apr. 25, 2011.

European Search Report for corresponding EP06737699 date of mailing is Feb. 12, 2012 (3 pgs).

* cited by examiner

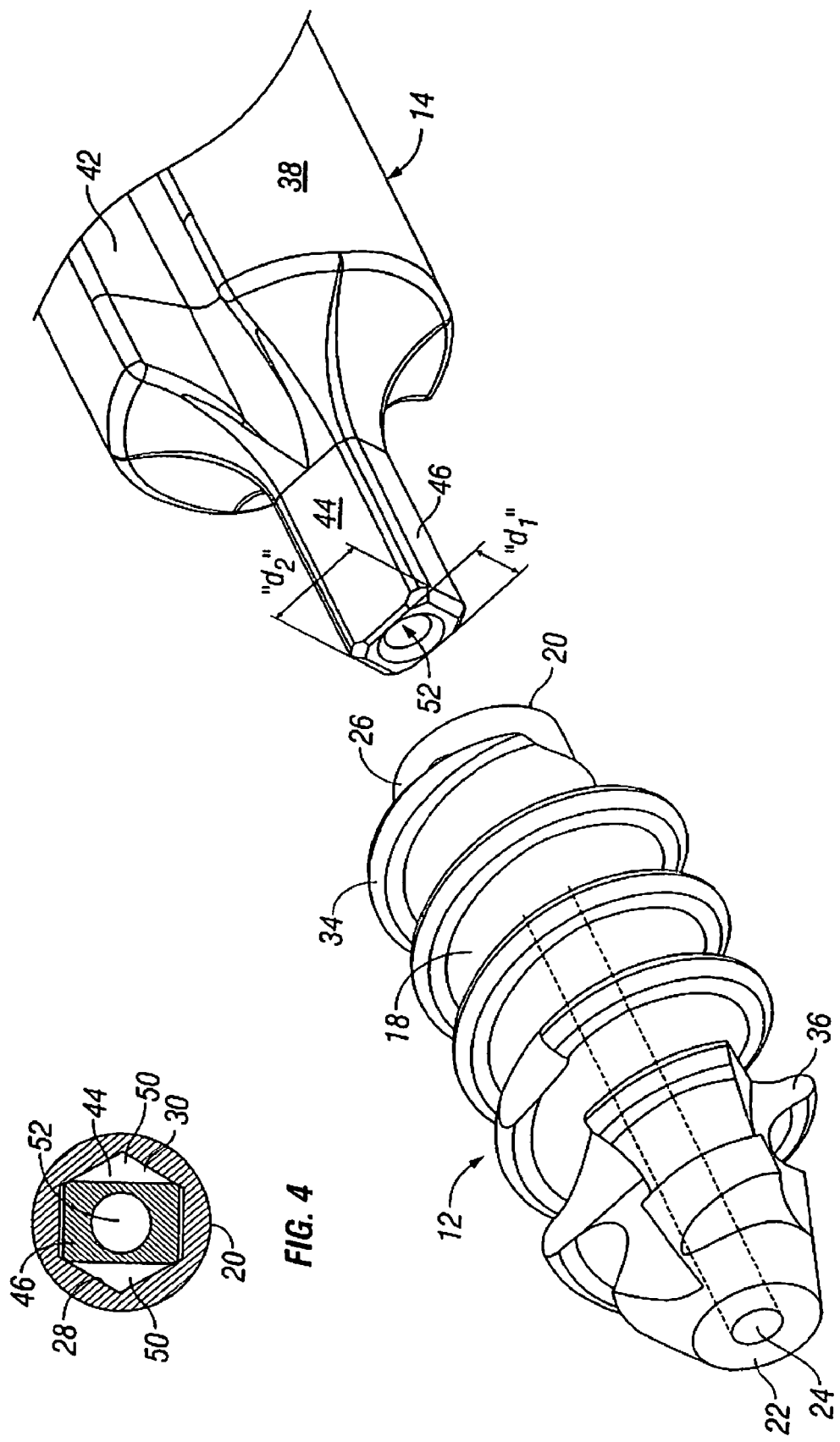

CANNULATED SUTURE ANCHOR SYSTEM

CROSS-REFERENCE TO RELATED APPLICATIONS

This application is a continuation of U.S. application Ser. No. 11/371,754, filed Mar. 9, 2006, now abandoned, the entire contents of which are incorporated by reference herein.

BACKGROUND OF THE INVENTION

1. Field of the Disclosure

The present disclosure relates to orthopedic surgery and, more particularly, relates to a system and method for performing arthroscopy shoulder repair.

2. Description of the Related Art

Shoulder arthroscopy involves the repair of tissue inside or around the shoulder joint. The procedure is typically performed under endoscopic visualization with, e.g., an arthroscope, which is introduced within a small incision in the skin. Various narrow diameter instruments are positioned within the tissue to perform the desired surgical procedure. A saline solution may be pumped into the shoulder to expand the joint to enhance visualization and facilitate manipulation of the instruments during the procedure.

Common shoulder injuries requiring arthroscopy include a torn or damaged cartilage ring (labrum) or ligaments causing shoulder instability, a torn rotator cuff or a torn or damaged biceps tendon. Each of these injuries necessitates the reattachment of soft tissue, e.g., the ligaments or tendons, to bone. Various fixation devices and methodologies including sutures, screws, staples, wedges and plugs are known to effectuate the attachment. Most of these fixation devices have proven to be generally adequate for their intended purposes.

SUMMARY OF THE INVENTION

Accordingly, the present disclosure is directed to further improvements in arthroscopic repair, particularly, repair of the shoulder. In one embodiment, a system and associated method for arthroscopic repair is particularly adapted in reattaching a ligament and/or tendon to cortical bone of the shoulder. In accordance with this preferred embodiment, a suture anchor system includes a suture anchor, preferably, a screw anchor, and an installation tool for installing the suture anchor in tissue. The suture anchor defines a longitudinal axis and has a longitudinal cannulation for reception and passage of a guide wire. The suture anchor has trailing and leading ends, and an anchor head adjacent the trailing end thereof. The anchor head includes at least one eyelet for reception of a suture and an internal bore therein.

The installation tool includes a main body and a driver head extending from the main body. The main body includes an outer surface having a longitudinal recess therein to accommodate the suture. The driver head is correspondingly dimensioned to be received within the internal bore of the anchor head of the suture anchor whereby movement of the installation tool about a longitudinal axis, e.g., rotational movement, thereof causes corresponding movement, e.g., rotational, of the suture anchor. The installation tool may also define a longitudinal cannulation for reception and passage of the guide wire.

In one preferred embodiment, the anchor head preferably includes first and second eyelets for reception of respective sutures. With this arrangement, the outer surface of the installation tool includes first and second longitudinal recesses for receiving respective sutures extending from the respective first and second eyelets of the anchor head. The first and second longitudinal recesses of the installation tool are in general alignment with the first and second eyelets of the anchor head when the suture anchor is mounted to the installation tool. In addition, the driver head of the installation tool may be dimensioned to define first and second clearances between respective outer surfaces of the driver head and internal surfaces of the internal bore of the anchor head when the driver head is mounted within the anchor head. The clearances accommodate suture portions of the sutures and are in general alignment with respective longitudinal recesses in the outer surface of the installation tool.

The arrangement of the eyelets, longitudinal recesses of the installation tool and sutures within the recesses significantly reduces the profile of the system to thereby facilitate maneuvering of the system within the restricted surgical area. In addition, with the sutures accommodated within the recesses, the potential of entanglement of the sutures during manipulation and/or rotation of the insertion tool is greatly minimized.

A method for attaching soft tissue to bone tissue within a bone area of a patient is also disclosed. The method includes the steps of:

accessing an internal target of a bone area of a patient, preferably, the shoulder area;

positioning a guide wire in relation to the internal target of the shoulder area;

mounting a cannulated anchor, preferably, a screw anchor onto the guide wire, the cannulated anchor having at least one suture connected thereto;

advancing the cannulated anchor along the guide wire to the internal target;

securing the cannulated anchor within bone tissue of the internal target; and securing soft tissue to the cannulated anchor with the at least one suture.

BRIEF DESCRIPTION OF THE DRAWINGS

Preferred embodiments of the present disclosure will be more readily appreciated by reference to the drawings wherein:

FIGS. 1-3 are perspective views of the suture anchor system of the present disclosure;

FIG. 4 is a cross-sectional view taken along the lines 4-4 of FIG. 1 illustrating the arrangement of the insertion tool within the screw head of the screw anchor.

DETAILED DESCRIPTION OF THE PREFERRED EMBODIMENTS

The suture anchor system of the present disclosure is intended for use in arthroscopic procedures and has particular application in securing soft tissue including tendons, ligaments etc. to hard cortical bone. The system may be used in conjunction with surgery performed on the knee, back, ankle, elbow etc. and has particular application in shoulder repair, particularly, arthroscopic shoulder repair. Such shoulder repair operations are inclusive, but, not limited to, reattachment of a torn or damaged cartilage ring (labrum) or ligaments, reattachment of a torn rotator cuff or reattachment of a torn or damaged biceps tendon. Other procedures are also envisioned.

Figure 1:
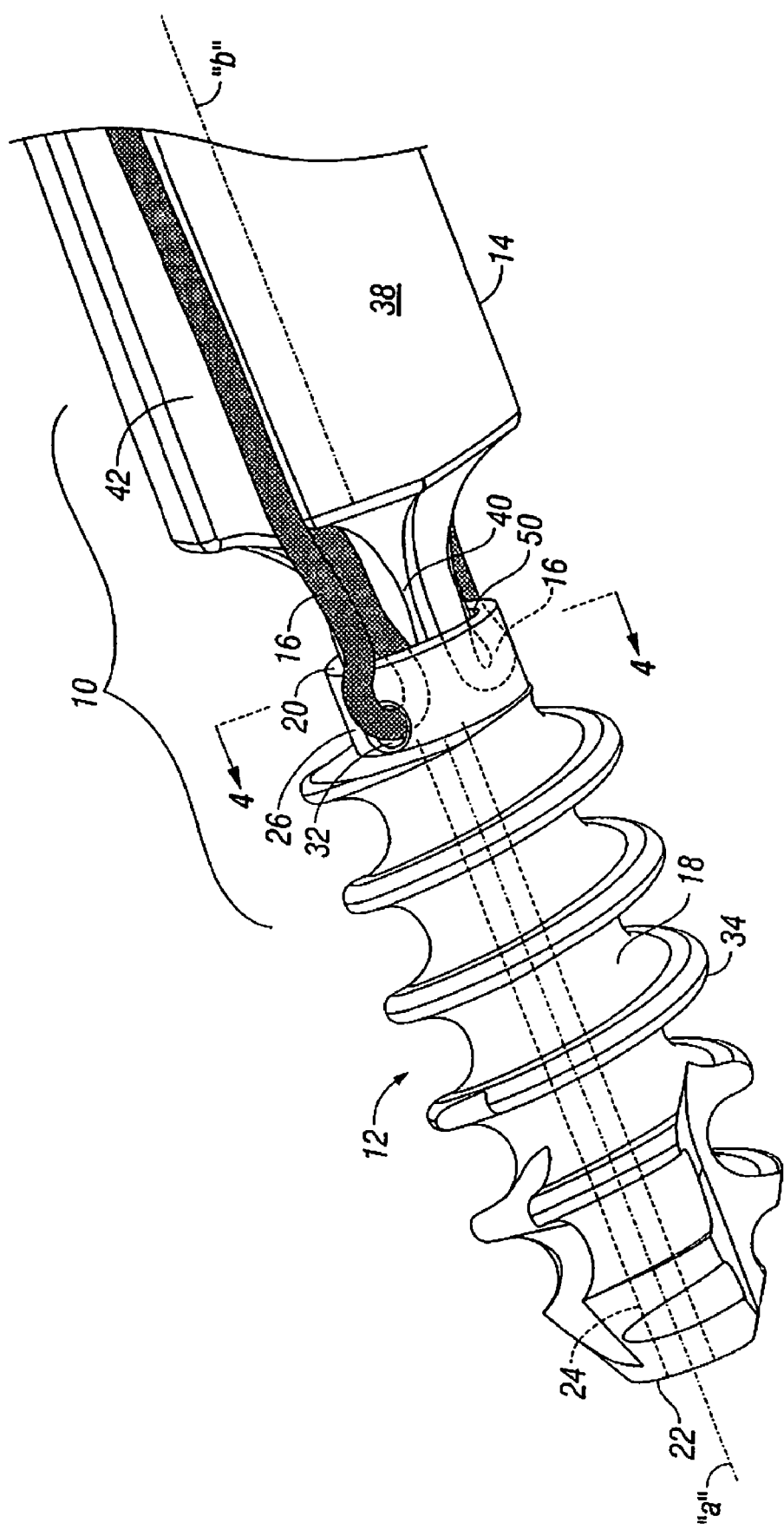
Figure 2:
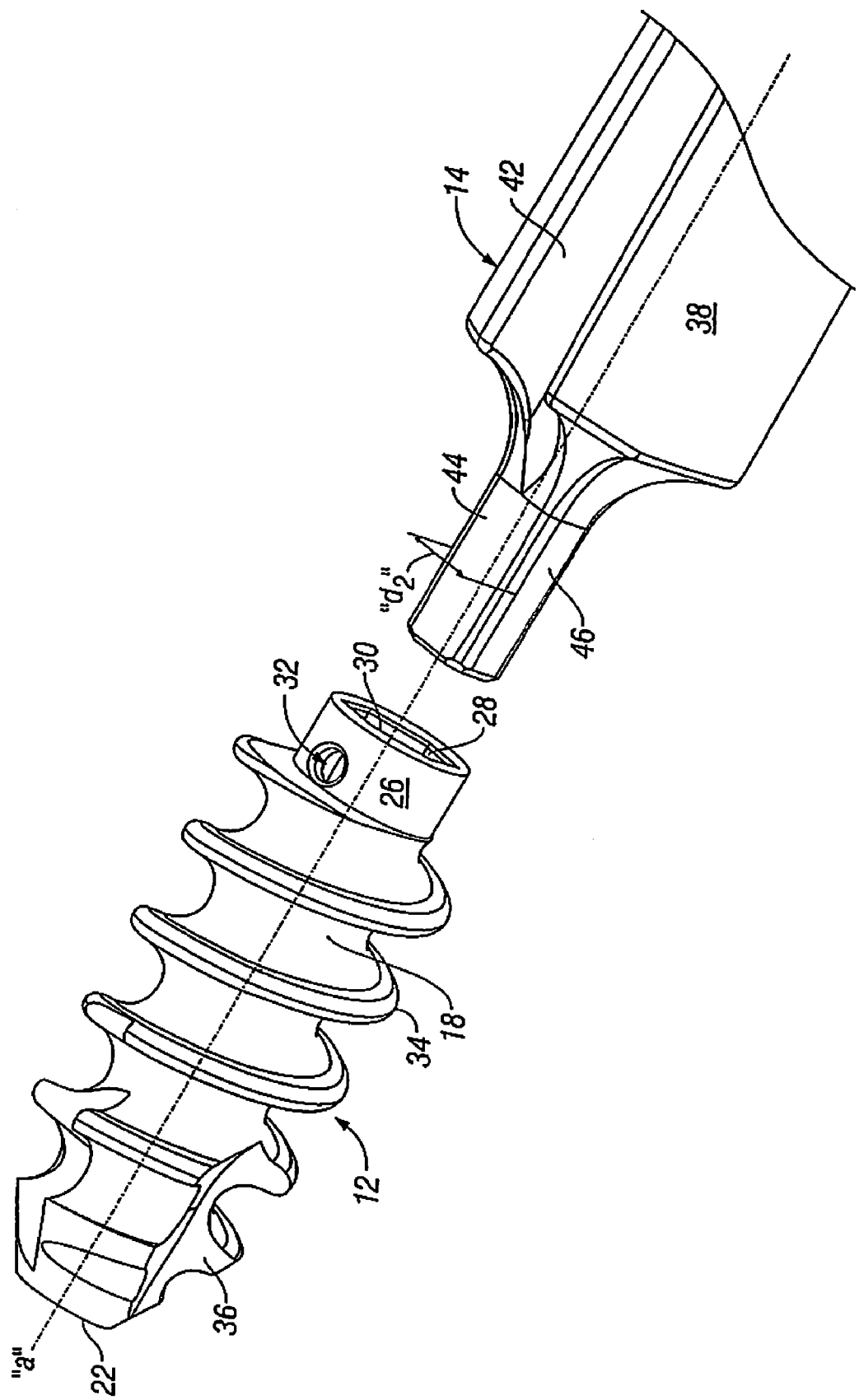

Referring now to the drawings wherein like reference numerals identify similar or like elements throughout the several views, FIGS. 1-3 illustrate, each in perspective view, the novel suture anchor system in accordance with the principles of the present disclosure. Suture anchor system 10 generally includes three components, namely screw anchor 12, insertion tool 14 for mounting the screw anchor 12 into bone and a pair of sutures 16 connected to the screw anchor 12 for securing the soft tissue to the screw anchor 12.

Screw anchor 12 includes anchor body 18 defining longitudinal axis "a" and having leading and trailing ends 20, 22. Anchor body 18 includes longitudinal cannulation 24 which extends the length of the anchor body 18. Cannulation 24 is dimensioned to receive a guide wire. Anchor body 18 further includes screw head 26 adjacent leading end 20. Screw head 26 includes inner wall portions 28 defining internal bore 30 which communicates with cannulation 24 (FIG. 4). Screw head 26 further has first and second diametrically opposed eyelets 32 which extend through the outer wall of the screw head 26. Internal bore 30 is dimensioned to cooperate with insertion tool 14. Although internal bore 30 may take various geometrical shapes including, e.g., square, rectangular, triangular or any other polygonal arrangement, in a preferred embodiment, the internal bore 30 is generally of hexagonal configuration. First and second eyelets 32 are adapted to receive sutures 16.

With reference again to FIGS. 1-3, anchor body 18 has an external thread 34 commencing adjacent screw head 26 and terminating in leading end 22. External thread 34 may be continuous along the length of anchor body 18 or alternatively be interrupted to define a plurality of thread segments. External thread 34 is preferably self-tapping although it is envisioned that the external thread may be configured for advancement within a pre-tapped bore in bone. External thread 34 further includes a plurality of flutes or cut-outs 36 in the thread. Flutes 36 collect bone tissue during the initial self-tapping advancement of the anchor body to facilitate the anchoring process.

Sutures 16 may be fabricated from any biocompatible material. The preferred materials for sutures 16 include synthetic bioabsorbable materials such as polymers or copolymers of glycolide, lactide, trimethylene carbonate, dioxanone, caprolactone or blends thereof. Other suitable materials for the components of sutures 16 include nonabsorbable materials such as polycarbonate, polyester, polyethylene, polyamide, polypropylene, polytetrafluoroethylene (PTFE), polysulfone and acrylic.

Referring still to FIGS. 1-3, insertion tool 14 will be discussed. Insertion tool 14 includes main body 38 defining longitudinal axis "b" and having driver head 40 at the end of the main body 38. It is noted that in the Figures only the distal end portion of main body 38 is illustrated. Main body 38 includes a pair of longitudinal recesses 42 within the outer surface of the main body 38 and extending from driver head 40 along at least a portion of the length preferably, the entire length of the main body 38. Longitudinal recesses 42 define an arc section removed from the outer surface of main body 38. The radius of the arc section preferably at least approximates the diameter of the sutures 16 to ensure that the sutures are fully accommodated within the longitudinal recesses during use of the system 10. Preferably, longitudinal recesses 42 are arranged in diametrical opposed relation as shown and are in alignment with eyelets 32 of anchor screw 14 when the anchor screw 12 is mounted to insertion tool 14 as depicted in FIG. 1.

As best depicted in FIGS. 3-4, driver head 40 defines a general rectangular cross-section having first and second cross-sectional dimensions "d1, d2" each being transverse to longitudinal axis "b". Second cross-sectional dimension "d2" is greater than first cross-sectional dimension "d1". Driver head 40 includes opposed outer surfaces 44 and opposed outer surfaces 46, and chamfered surfaces 48 interconnecting the surfaces 44, 46. When driver head 40 is mounted within screw head 26, a clearance or gap 50 is defined between outer surfaces 44 and inner surface portions 30 of the screw head 26. (FIG. 4) The clearances 50 are in general longitudinal alignment with respective eyelets 32 of screw head 26 and respective longitudinal recesses 42 of insertion tool 14. The distances between inner surface portions 30 and surfaces 44 within clearances 50 are each preferably dimensioned to at least be equal to, preferably, slightly greater than, the diameters of sutures 16. With this arrangement, the sutures 16 may slide within the clearance area 50 during manipulation of the system 10. Furthermore, the overall axial profile of system 10 is reduced by virtue of longitudinal recesses 42 to facilitate use during a minimally invasive or laparoscopic procedure.

Insertion tool 14 further defines longitudinal cannulation 52 extending along the length of the insertion tool 14. Longitudinal cannulation 52 is dimensioned for receiving a guide wire.

The use of the system 10 during repair of a detached soft tissue in the shoulder will now be discussed. The following discussion of the use of the system will be described in terms of the performance of an arthroscopic procedure within the shoulder, particularly, a procedure utilizing reattaching soft tissue, e.g., a tendon or ligament to cortical bone in the shoulder. Such tendon or ligament may be the labrum, rotator cuff or biceps tendon.

Figure 5:
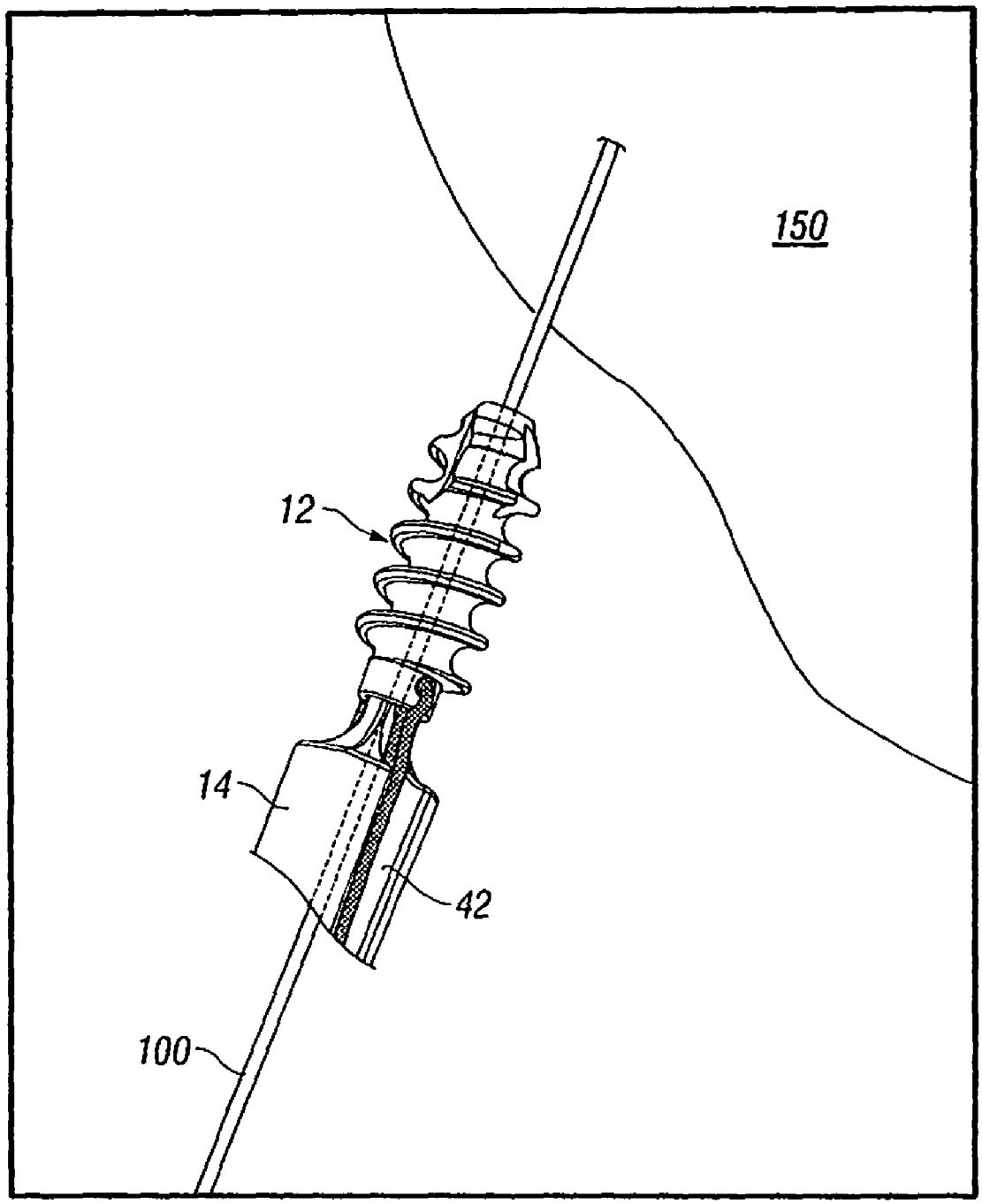
FIGS. 5-6 illustrate a preferred method of use of the suture anchor system in shoulder repair.

Referring now to FIG. 5, an internal target area is accessed through a small incision in the tissue adjacent the shoulder. An arthroscope may be utilized and introduced through a cannula as is conventional in the art to visualize the target area. Saline solution may then be pumped within the shoulder joint to expand the joint to provide more room to perform the procedure. A guide wire 100 is advanced through the shoulder joint to contact the cortical bone 150. The guide wire 100 may be at least partially embedded within the cortical bone 150 to positively fix the guide wire 100 to facilitate advancement of the remaining instruments. The guide wire 100 may be driven into the cortical bone 100 or alternatively, a drill may be introduced through a cannula to drill a bore for reception of the distal end of the guide wire. The guide wire 100 may optionally be driven through the tendon/ligament to be reattached and then secured to the cortical bone as discussed hereinabove.

With the guide wire 100 secured within the cortical bone 150, a cannulated drill (not shown) may be advanced along the guide wire 100 to core a hole in the targeted cortical bone 150 for subsequent positioning of screw anchor 12. The hole within the cortical bone may be tapped if desired with a tapping instrument. The screw anchor 12 with mounted insertion tool 14 are positioned over the guide wire 100 with the guide wire 100 being accommodated within cannulations 24, 52 of the screw anchor 12 and the insertion tool 14, respectively.

Figure 6:
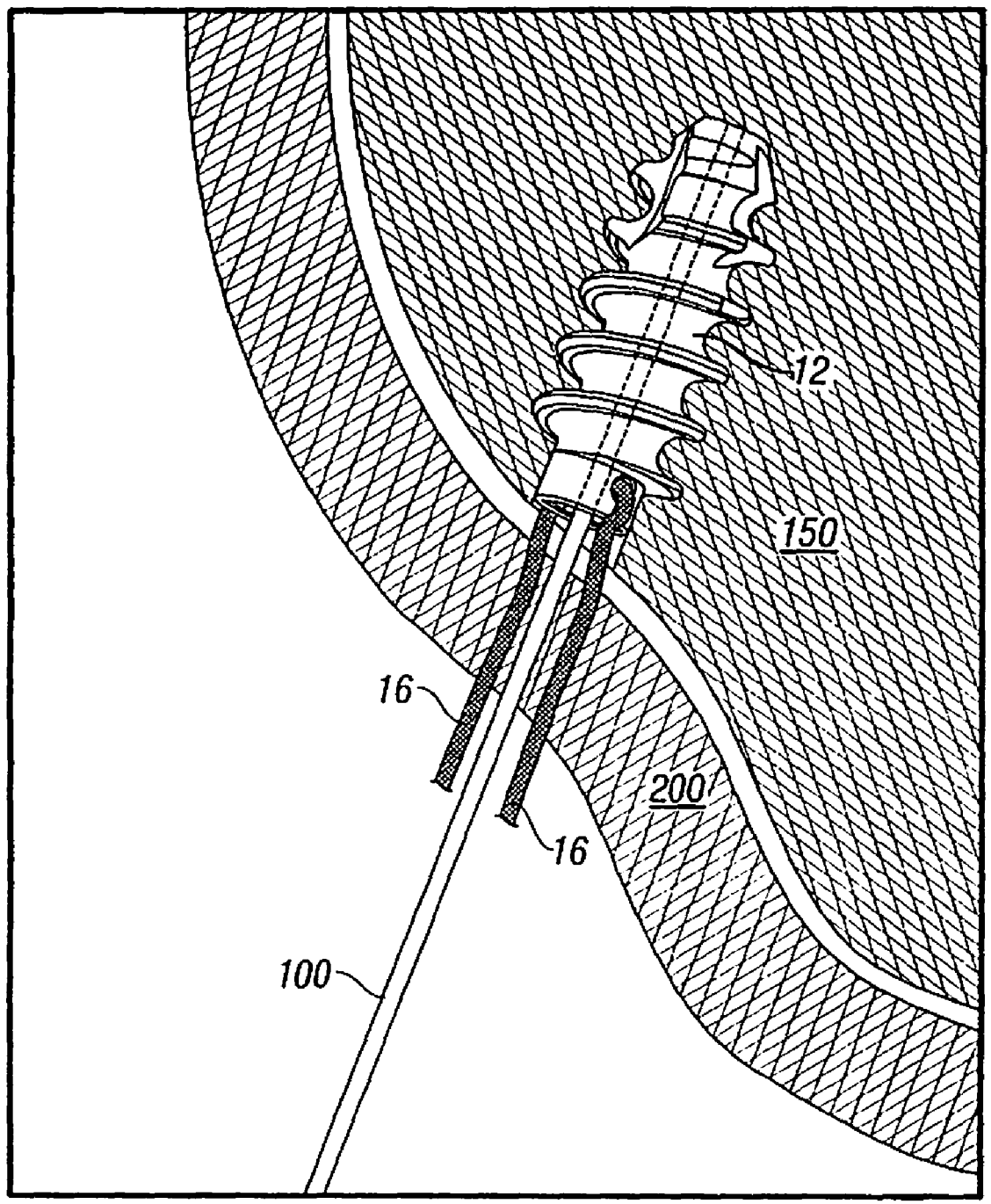

With reference now to FIG. 6, the screw anchor 12 is positioned within the hole in the cortical bone 150 by rotating the insertion tool 14 to cause corresponding rotational movement of the screw anchor 12 to advance the screw anchor 12 within the cortical bone 150. Once the screw anchor 12 is secured in place within the bone, the guide wire 100 is removed. Sutures 16 are then passed through the tendon/ligament 200 and tied off (by knotting) to secure the ligament 200 to the screw anchor 12 and cortical bone 150. It is appreciated that sutures 16 may be passed through the tendon/ligament 200 and then loaded onto suture anchor 16 followed by placement of the screw anchor 12 in the cortical bone if desired. As a further alternative, the screw anchor 12 with mounted sutures 16 may be punched through the tendon/ligament 200 and advanced within the cortical bone 150 followed by subsequent tying-off of the sutures 16. Over time, sufficient tissue growth/regrowth occurs to affix the natural tendon/ligament 200 to the cortical bone.

As appreciated, during advancement and rotation of insertion tool 14 and screw anchor 12, sutures 16 are accommodated within longitudinal recesses 42 of the insertion tool 14. Thus, the overall profile of the system is reduced. Moreover, with the sutures 16 accommodated within the longitudinal recesses 42, the potential of entanglement of the sutures 16 is significantly reduced during rotational movement of the insertion tool 14.

While the invention has been particularly shown, and described with reference to the preferred embodiments, it will be understood by those skilled in the art that various modifications and changes in form and detail may be made therein without departing from the scope and spirit of the invention. For example, the system and method for shoulder repair may incorporate a screwless anchor, i.e., an anchor devoid of an external screw thread. Anchors suitable for this purpose are disclosed in commonly assigned U.S. Pat. No. 5,720,753 to Sander et al. and U.S. Pat. No. 5,948,000 to Larsen et al., the contents of each being incorporated herein by reference. The anchors disclosed in the '753 and '000 patents incorporate expandable legs with anchoring means to engage the bone and may be deployed through non rotational longitudinal movement of a drive element. Another anchor which may be adapted for use in the system and method of shoulder repair of the present invention is disclosed in U.S. Pat. No. 5,980,558 to Wiley, the contents of which are incorporated herein by reference. The anchor disclosed in the '558 patent incorporates a rigid spear for driving into the bone and a plurality of wings which engage the bone upon deployment with a drive instrument.

Other modifications such as those suggested above, but not limited thereto, are to be considered within the scope of the invention.

What is claimed is:

1. A method for attaching soft tissue to bone tissue within a bone of a patient, comprising the steps of:
   accessing an internal target of a bone area of a patient;
   positioning a guide wire in relation to the internal target of the bone area;
   mounting a cannulated anchor onto the guide wire, the cannulated anchor including a threaded shaft and a threadless anchor head, and defining a longitudinal axis, the shaft and the anchor head defining an internal bore for receiving the guide wire, the anchor head defining first and second eyelets, the anchor head and the first and second eyelets being disposed proximal of the shaft, the cannulated anchor having at least a portion of a first suture and at least a portion of a second suture passed through respective first and second eyelets;
   advancing the cannulated anchor along the guide wire to the internal target;
   engaging the anchor head with a driver head of an installation tool, the anchor head and the driver head forming first and second clearances defined between respective first and second exterior side surfaces of the driver head and respective first and second interior surfaces of the internal bore;
   positioning first and second sutures through respective first and second clearances and within first and second longitudinal recesses defined along the exterior surface of the installation tool, respectively;
   securing the cannulated anchor within bone tissue of the internal target; and
   attaching soft tissue to the cannulated anchor with at least one of the first and second sutures.

2. The method according to claim 1 wherein the step of securing the cannulated anchor includes rotating the cannulated anchor to engage and advance the threaded shaft within the bone tissue.

3. The method according to claim 2 wherein the step of securing the cannulated anchor includes mounting the installation tool within the internal bore of the cannulated anchor and onto the guide wire and rotating the installation tool to cause corresponding rotational movement of the cannulated anchor.

4. The method according to claim 3 wherein the step of securing the cannulated anchor includes securing the first and second sutures relative to the first and second eyelets of the anchor head.

5. The method according to claim 1 wherein the step of positioning the guide wire includes advancing the guide wire to contact the bone tissue.

6. The method according to claim 5 wherein the step of advancing the guide wire includes embedding at least a portion of the guide wire into the bone tissue.

7. The method according to claim 1 wherein the internal target includes the shoulder area of the patient and the step of accessing includes accessing the shoulder area.

8. The method according to claim 1 wherein the first and second eyelets of the cannulated anchor are in general longitudinal alignment with respective first and second longitudinal recesses of the insertion tool whereby, during the step of positioning, suture portions of each of the first and second sutures are in substantial longitudinal alignment with the first and second longitudinal recesses.

9. The method according to claim 8 wherein the first and second longitudinal recesses of the insertion tool stand along a major portion of the length of the insertion tool whereby, during the step of securing, the potential for entanglement of the first and second sutures is substantially minimized.

10. A method for attaching soft tissue to bone tissue within a bone of a patient, comprising the steps of
   accessing an internal target of a bone area of a patient;
   positioning a guide wire in relation to the internal target of the bone area;
   mounting a cannulated anchor onto the guide wire, the cannulated anchor including a threaded shaft and an anchor head, and defining a longitudinal axis, defining first and second eyelets, the anchor head and the first and second eyelets being disposed proximal of the shaft;
   introducing the guide wire though a longitudinal bore of the cannulated anchor and advancing the cannulated anchor along the guide wire to the internal target;
   positioning a driver head of an installation tool within the anchor head, the anchor head and the driver head forming first and second clearances defined between respective first and second exterior side surfaces of the driver head and respective first and second interior surfaces of the anchor head, the installation tool including first and second longitudinal recesses defined along the exterior surface of the installation tool and being in general longitudinal alignment with respective first and second eyelets of the anchor head;
   passing respective first and second sutures through the first and second eyelets to extend through the first and second clearances and within respective first and second longitudinal recesses of the insertion tool;

rotating the insertion tool to cause corresponding rotation of the threaded shaft of the cannulated anchor to secure the cannulated anchor relative to bone tissue of the internal target; and attaching soft tissue to the cannulated anchor by passing suture portions of the first and second sutures through tissue and securing the first and second sutures relative to the first and second eyelets.

* * * * *